United States Patent
Wideman et al.

[11] Patent Number: 6,040,389
[45] Date of Patent: Mar. 21, 2000

[54] BIS(HYDROXYALKYL ALKYL ESTER) POLYSULFIDES

[75] Inventors: Lawson Gibson Wideman, Hudson; Paul Harry Sandstrom, Tallmadge, both of Ohio

[73] Assignee: The Goodyear Tire & Rubber Company, Akron, Ohio

[21] Appl. No.: 09/086,216

[22] Filed: May 28, 1998

[51] Int. Cl.[7] .............................. C08C 19/20; C08K 3/36; C08K 3/04; B60C 11/00
[52] U.S. Cl. ...................... 525/332.6; 524/262; 524/492; 524/495; 152/209 RR
[58] Field of Search ........................ 525/332.6; 524/262, 524/492, 495; 152/209 RR

[56] References Cited

U.S. PATENT DOCUMENTS

| | | | |
|---|---|---|---|
| 3,873,489 | 3/1975 | Thurn et al. | 524/262 |
| 5,347,015 | 9/1994 | Keller et al. | 548/455 |
| 5,407,972 | 4/1995 | Smith et al. | 522/96 |
| 5,504,137 | 4/1996 | Sandstrom et al. | 524/492 |
| 5,804,619 | 9/1998 | Nicol et al. | 525/289 |

FOREIGN PATENT DOCUMENTS

| | | |
|---|---|---|
| 0529373 | 8/1992 | European Pat. Off. . |
| 0791622 | 2/1997 | European Pat. Off. . |

*Primary Examiner*—Tae Yoon
*Attorney, Agent, or Firm*—Bruce J Hendricks

[57] ABSTRACT

The present invention relates to bis(hydroxyalkyl alkyl ester) polysulfides of the formula

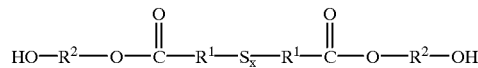

where $R^1$ is independently selected from alkylene groups having 1 to 8 carbon atoms, $R^2$ is independently selected from alkylene groups having 2 to 6 carbon atoms and x is an integer of from 2 to 8. These polysulfides are particularly suited for use in rubber compositions.

12 Claims, No Drawings

BIS(HYDROXYALKYL ALKY LESTER) POLYSULFIDES

FIELD OF THE INVENTION

The present invention relates to bis(hydroxyalkyl alkyl ester) polysulfides and its use in rubber compositions.

BACKGROUND OF THE INVENTION

Sulfur containing organosilicon compounds are useful as reactive coupling agents between rubber and silica fillers providing for improved physical properties. They are also useful as adhesion primers for glass, metals and other substrates.

U.S. Pat. Nos. 3,842,111 and 3,873,489 disclose various sulfur containing organosilicon compounds. These sulfur containing organosilicon compounds are of the formula

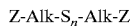

Z-Alk-S$_n$-Alk-Z where Z is

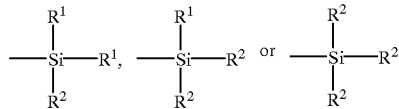

where $R^1$ is an alkyl of 1 to 4 carbon atoms or phenyl and $R^2$ is alkoxy of 1 to 8 carbon atoms, cycloalkoxy of 5 to 8 carbon atoms; or alkylmercapto with 1 to 8 carbon atoms; Alk is a divalent aliphatic hydrocarbon or unsaturated aliphatic hydrocarbon or a cyclic hydrocarbon containing 1 to 18 carbon atoms and n is an integer of from 2 to 6.

Japanese Application J6 2115045-A discloses rubber compositions containing disulfide compounds of the formula

R—S—S—R where R can be 1–18 carbon allyl, (ar)alkyl or alkanyl optionally substituted with carboxyl, alkoxycarbonyl, N-alkylamido, N-anilinoamide and amino.

U.S. Pat. No. 5,347,015 relates to disulfides of the formula

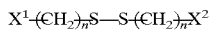

X$^1$-(CH$_2$)$_n$-S—S-(CH$_2$)$_n$-X$^2$ where $X^1$ and $X^2$ are identical to one another and are each —Br, —N—phthalimide, —NH$_2$, —OOC-(CH$_2$)$_3$COOH, —OSO$_2$—CH$_3$, —NH-(CH$_2$)$_2$NH$_2$, —SO$_3$H or —SO$_3^-$ M$^+$ and n is from 11 to 25 or $X^1$ is —OH and $X^2$ is —Br or $X^1$ and $X^2$ are each —COO—CH$_2$—CH$_3$ and n is 10 to 25.

SUMMARY OF THE INVENTION

The present invention relates to bis(hydroxyalkyl alkyl ester) polysulfides and its use in rubber.

DETAILED DESCRIPTION OF THE INVENTION

There is disclosed a bis(hydroxyalkyl alkyl ester) polysulfide of the formula

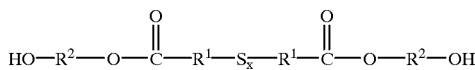

where $R^1$ is independently selected from alkylene groups having 1 to 8 carbon atoms, $R^2$ is independently selected from alkylene groups having 2 to 6 carbon atoms and x is an integer of from 2 to 8.

In addition, there is disclosed an elastomer containing olefinic unsaturation and a bis(hydroxyalkyl alkyl ester) polysulfide of the formula

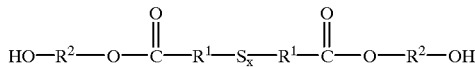

where $R^1$ is independently selected from alkylene groups having 1 to 8 carbon atoms, $R^2$ is independently selected from alkylene groups having 2 to 6 carbon atoms and x is an integer of from 2 to 8.

The present invention may be used to process sulfur vulcanizable rubbers or elastomers containing olefinic unsaturation. The phrase "rubber or elastomer containing olefinic unsaturation" is intended to include both natural rubber and its various raw and reclaim forms as well as various synthetic rubbers. In the description of this invention, the terms "rubber" and "elastomer" may be used interchangeably, unless otherwise prescribed. The terms "rubber composition," "compounded rubber" and "rubber compound" are used interchangeably to refer to rubber which has been blended or mixed with various ingredients and materials and such terms are well known to those having skill in the rubber mixing or rubber compounding art. Representative synthetic polymers are the homopolymerization products of butadiene and its homologues and derivatives, for example, methylbutadiene, dimethylbutadiene and pentadiene as well as copolymers such as those formed from butadiene or its homologues or derivatives with other unsaturated monomers. Among the latter are acetylenes, for example, vinyl acetylene; olefins, for example, isobutylene, which copolymerizes with isoprene to form butyl rubber; vinyl compounds, for example, acrylic acid, acrylonitrile (which polymerize with butadiene to form NBR), methacrylic acid and styrene, the latter compound polymerizing with butadiene to form SBR, as well as vinyl esters and various unsaturated aldehydes, ketones and ethers, e.g., acrolein, methyl isopropenyl ketone and vinylethyl ether. Specific examples of synthetic rubbers include neoprene (polychloroprene), polybutadiene (including cis-1,4-polybutadiene), polyisoprene (including cis-1,4-polyisoprene), butyl rubber, styrene/isoprene/butadiene rubber, copolymers of 1,3-butadiene or isoprene with monomers such as styrene, acrylonitrile and methyl methacrylate, as well as ethylene/propylene terpolymers, also known as ethylene/propylene/diene monomer (EPDM), and in particular, ethylene/propylene/dicyclopentadiene terpolymers. The preferred rubber or elastomers are polybutadiene and SBR.

In one aspect the rubber is preferably of at least two of diene based rubbers. For example, a combination of two or more rubbers is preferred such as cis 1,4-polyisoprene rubber (natural or synthetic, although natural is preferred), 3,4-polyisoprene rubber, styrene/isoprene/butadiene rubber, emulsion and solution polymerization derived styrene/butadiene rubbers, cis 1,4-polybutadiene rubbers and emulsion polymerization prepared butadiene/acrylonitrile copolymers.

In one aspect of this invention, an emulsion polymerization derived styrene/butadiene (E-SBR) might be used having a relatively conventional styrene content of about 20 to about 28 percent bound styrene or, for some applications, an E-SBR having a medium to relatively high bound styrene content, namely, a bound styrene content of about 30 to about 45 percent.

The relatively high styrene content of about 30 to about 45 for the E-SBR can be considered beneficial for a purpose of enhancing traction, or skid resistance, of the tire tread. The presence of the E-SBR itself is considered beneficial for a purpose of enhancing processability of the uncured elastomer composition mixture, especially in comparison to a utilization of a solution polymerization prepared SBR (S-SBR).

By emulsion polymerization prepared E-SBR, it is meant that styrene and 1,3-butadiene are copolymerized as an aqueous emulsion. Such are well known to those skilled in such art. The bound styrene content can vary, for example, from about 5 to about 50 percent. In one aspect, the E-SBR may also contain acrylonitrile to form a terpolymer rubber, as E-SBAR, in amounts, for example, of about 2 to about 30 weight percent bound acrylonitrile in the terpolymer.

Emulsion polymerization prepared styrene/butadiene/acrylonitrile copolymer rubbers containing about 2 to about 40 weight percent bound acrylonitrile in the copolymer are also contemplated as diene based rubbers for use in this invention.

The solution polymerization prepared SBR (S-SBR) typically has a bound styrene content in a range of about 5 to about 50, preferably about 9 to about 36, percent. The S-SBR can be conveniently prepared, for example, by organo lithium catalyzation in the presence of an organic hydrocarbon solvent.

A purpose of using S-SBR is for improved tire rolling resistance as a result of lower hysteresis when it is used in a tire tread composition.

The 3,4-polyisoprene rubber (3,4-PI) is considered beneficial for a purpose of enhancing the tire's traction when it is used in a tire tread composition. The 3,4-PI and use thereof is more fully described in U.S. Pat. No. 5,087,668 which is incorporated herein by reference. The Tg refers to the glass transition temperature which can conveniently be determined by a differential scanning calorimeter at a heating rate of 10° C. per minute.

The cis 1,4-polybutadiene rubber (BR) is considered to be beneficial for a purpose of enhancing the tire tread's wear, or treadwear. Such BR can be prepared, for example, by organic solution polymerization of 1,3-butadiene. The BR may be conveniently characterized, for example, by having at least a 90 percent cis 1,4-content.

The cis 1,4-polyisoprene and cis 1,4-polyisoprene natural rubber are well known to those having skill in the rubber art.

The term "phr" as used herein, and according to conventional practice, refers to "parts by weight of a respective material per 100 parts by weight of rubber, or elastomer."

The bis(hydroxyalkyl alkyl ester) polysulfides of the present invention are of the formula

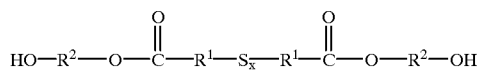

where $R^1$ is independently selected from alkylene groups having from 1 to 8 carbon atoms and $R^2$ is independently selected from alkylene groups having 2 to 6 carbon atoms and x is an integer of from 2 to 8 and x is an integer ranging from 2 to 8. Preferably, each $R^1$ is an alkylene group having from 1 to 6 carbon atoms, $R^2$ is an alkylene group having from 2 to 4 carbon atoms and x is an integer of from 2 to 4. Depending on the method of production, the bis(hydroxyalkyl alkyl ester) polysulfides may comprise a high purity product or mixture of products. For example, it is contemplated herein that not only high purity bis(hydroxyalkyl alkyl ester) polysulfides of the above formula may be used but also mixtures of bis(hydroxyalkyl alkyl ester) polysulfides of the above formula may be used, such as where some of the bis(hydroxyalkyl alkyl ester) polysulfides have two sulfur atoms, some have four, some have six sulfur atoms and the like.

The bis(hydroxyalkyl alkyl ester) polysulfides may be prepared by reacting a compound of the formula:

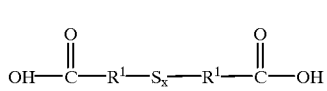

II where $R^1$ and x are as defined above, with a compound of the formula:

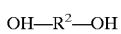

III where $R^2$ is as defined above.

Examples of suitable starting materials of Formula II include 3,3'-dithiodipropionic acid, 3,3'-tetrathiodipropionic acid, 3,3'-hexathiodipropionic acid, 3,3'-octathiodipropionic acid and mixtures thereof, and 4,4'-dithiodibutyric acid and so forth.

Example of suitable starting materials of Formula III include ethylene glycol, propylene glycol, butane diol, pentanediol and hexanediol.

The mole ratio of the compound of formula II to the compound of formula III may vary from 0.5:2 to 2:0.5. Preferably, the mole ratio ranges from 1:1 to 1:2.

An organic solvent may be used to dissolve the acid of Formula II to increase heat transfer and to facilitate water removal through a reflux trap. The solvent is preferably inert to the esterification reaction. Illustrative of solvents suitable for use in the practice of this invention include: saturated and aromatic hydrocarbons, e.g., hexane, octane, dodecane, naphtha, decalin, tetrahydronaphthalene, kerosene, mineral oil, cyclohexane, cycloheptane, alkyl cycloalkane, benzene, toluene, xylene, alkyl-naphthalene, and the like; ethers such as tetrahydrofuran, tetrahydropyran, diethylether, 1,2-dimethoxybenzene, 1,2-diethoxybenzene, the dialkylethers of ethylene glycol, propylene glycol, butylene glycol, diethylene glycol, dipropylene glycol, oxyethyleneoxypropylene glycol, and the like; fluorinated hydrocarbons that are inert under the reaction conditions such as perfluoroethane, monofluorobenzene, and the like. Another class of solvents are sulfones such as dimethylsulfone, diethylsulfone, diphenolsulfone, sulfolane, and the like. Mixtures of the aforementioned solvents may be employed so long as they are compatible with each other under the conditions of the reaction and will adequately dissolve the acid and glycol and not interfere with the esterification reaction.

The esterification reaction may be conducted in the presence of a catalyst to speed up the reaction. Examples of catalysts that may be used include condensation catalysts, e.g., dibutyltin oxide or butyl stannoic acid. In addition acid catalysts may be used such as sulfuric acid, hydrochloric acid and toluenesulfonic acid. The amount of catalyst that is used will vary depending on the particular catalyst that is selected. For example, when an acid catalyst is used, from about 5 weight percent to about 10 weight percent is recommended.

The esterification reaction may be conducted over a variety of temperature ranges. The temperatures may range from moderate to an elevated temperature. In general, the esterification reaction may be conducted at a temperature ranging from about 100° C. to about 250° C. The preferred temperature range is from about 110° C. to about 200° C. while the most preferred temperature range is from about 120° C. to about 190° C.

The esterification reaction may be conducted over a variety of pressures. Preferably the reaction is conducted at a pressure range of from about 0 to about 100 psig.

The esterification reaction is conducted for a period of time sufficient to produce the desired bis(hydroxyalkyl alkyl ester) polysulfides. In general, the reaction time can vary from minutes to several hours. If the more sluggish reaction conditions are selected, then the reaction time will have to be extended until the desired product is produced. It is appreciated that the residence time of the reactants will be influenced by the reaction temperature, concentration and choice of catalyst, if any, reaction pressure, concentration and choice of solvent, and other factors.

The esterification reaction may be carried out in a batch, semi-continuous or continuous manner. The esterification reaction may be conducted in a single reaction zone or in a plurality of reaction zones, in series or in parallel. The reaction may be conducted intermittently or continuously. The reaction may be conducted in a vessel equipped with a thermometer, stirrer and a distillation column to separate water that distills from reactants and optionally a Dean Stark trap. The reactor may be fitted with internal and/or external heat exchangers to control temperature fluctuations. Preferably, an agitation means is available to ensure a uniform reaction. Mixing induced by vibration, shaker, stirrer, rotating, oscillation, etc. are all illustrative of the types of agitation means which are contemplated for use in the esterification reaction. Such agitation means are available and well known to those skilled in the art.

The bis(hydroxyalkyl alkyl ester) polysulfide of the present invention may be added to the rubber by any conventional technique such as on a mill or in a Banbury. The amount of bis(hydroxyalkyl alkyl ester) polysulfide may vary widely depending on the type of rubber and other compounds present in the vulcanizable composition. Generally, the amount of bis(hydroxyalkyl alkyl ester) polysulfide is used in a range of from about 0.05 to about 10.0 phr with a range of 0.1 to about 5.0 phr being preferred. The bis(hydroxyalkyl alkyl ester) polysulfide is preferably added in the nonproductive stage with the silica and optional sulfur-containing organosilicon coupling agent.

For ease in handling, the bis(hydroxyalkyl alkyl ester) polysulfide may be used per se or may be deposited on suitable carriers. Examples of carriers which may be used in the present invention include silica, carbon black, alumina, kieselguhr, silica gel and calcium silicate.

The rubber composition may contain a sufficient amount of filler to contribute a reasonably high modulus and high resistance to tear. The total filler may be added in amounts ranging from 10 to 250 phr. When the filler includes silica, the silica is present in an amount ranging from 10 to 80 phr. Preferably, the amount of silica ranges from 15 to 50 phr. When the filler is carbon black, the amount of carbon black may vary. Generally speaking, the amount of carbon black, when used, will vary from 1 to 80 phr. Preferably, the amount of carbon black will range from 1 to 40 phr. It is to be appreciated that a silica coupler may be used in conjunction with a carbon black, namely pre-mixed with a carbon black prior to addition to the rubber composition, and such carbon black is to be included in the aforesaid amount of carbon black for the rubber composition formulation.

The commonly employed siliceous pigments used in rubber compounding applications can be used as the silica in this invention, including pyrogenic and precipitated siliceous pigments (silica), although precipitate silicas are preferred. The siliceous pigments preferably employed in this invention are precipitated silicas such as, for example, those obtained by the acidification of a soluble silicate, e.g., sodium silicate.

Such silicas might be characterized, for example, by having a BET surface area, as measured using nitrogen gas, preferably in the range of about 40 to about 600, and more usually in a range of about 50 to about 300 square meters per gram. The BET method of measuring surface area is described in the *Journal of the American Chemical Society*, Volume 60, page 304 (1930).

The silica may also be typically characterized by having a dibutylphthalate (DBP) absorption value in a range of about 100 to about 400, and more usually about 150 to about 300.

The silica might be expected to have an average ultimate particle size, for example, in the range of 0.01 to 0.05 micron as determined by the electron microscope, although the silica particles may be even smaller, or possibly larger, in size.

Various commercially available silicas may be considered for use in this invention such as, only for example herein, and without limitation, silicas commercially available from PPG Industries under the Hi-Sil trademark with designations 210, 243, etc; silicas available from Rhone-Poulenc, with, for example, designations of Z1165MP and Z165GR and silicas available from Degussa AG with, for example, designations VN2 and VN3, etc.

Whereas the bis(hydroxyalkyl alkyl ester) polysulfide functions as a silica coupling agent, the processing of the sulfur vulcanizable rubber may be conducted in the presence of a sulfur containing organosilicon compound. Examples of suitable sulfur containing organosilicon compounds are of the formula:

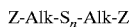

in which Z is selected from the group consisting of

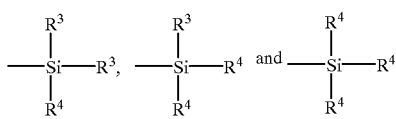

where $R^3$ is an alkyl group of 1 to 4 carbon atoms, cyclohexyl or phenyl;

$R^4$ is alkoxy of 1 to 8 carbon atoms, or cycloalkoxy of 5 to 8 carbon atoms;

Alk is a divalent hydrocarbon of 1 to 18 carbon atoms and n is an integer of 2 to 8.

Specific examples of sulfur containing organosilicon compounds which may be used in accordance with the present invention include: 3,3'-bis(trimethoxysilylpropyl) disulfide, 3,3'-bis(triethoxysilylpropyl) tetrasulfide, 3,3'-bis (triethoxysilylpropyl) octasulfide, 3,3'-bis (trimethoxysilylpropyl) tetrasulfide, 2,2'-bis (triethoxysilylethyl) tetrasulfide, 3,3'-bis (trimethoxysilylpropyl) trisulfide, 3,3'-bis (triethoxysilylpropyl) trisulfide, 3,3'-bis (tributoxysilylpropyl) disulfide, 3,3'-bis (trimethoxysilylpropyl) hexasulfide, 3,3'-bis (trimethoxysilylpropyl) octasulfide, 3,3'-bis (trioctoxysilylpropyl) tetrasulfide, 3,3'-bis (trihexoxysilylpropyl) disulfide, 3,3'-bis(tri-2"-ethylhexoxysilylpropyl) trisulfide, 3,3'-bis (triisooctoxysilylpropyl) tetrasulfide, 3,3'-bis(tri-t-butoxysilylpropyl) disulfide, 2,2'-bis (methoxy diethoxy silyl ethyl) tetrasulfide, 2,2'-bis(tripropoxysilylethyl) pentasulfide, 3,3'-bis(tricyclohexoxysilylpropyl) tetrasulfide, 3,3'-bis(tricyclopentoxysilylpropyl) trisulfide, 2,2'-bis(tri-2"-methylcyclohexoxysilylethyl) tetrasulfide, bis (trimethoxysilylmethyl) tetrasulfide, 3-methoxy ethoxy propoxysilyl 3'-diethoxybutoxy-silylpropyltetrasulfide, 2,2'-bis (dimethyl methoxysilylethyl) disulfide, 2,2'-bis(dimethyl sec.butoxysilylethyl) trisulfide, 3,3'-bis(methyl butylethoxysilylpropyl) tetrasulfide, 3,3'-bis(di t-butylmethoxysilylpropyl) tetrasulfide, 2,2'-bis(phenyl methyl methoxysilylethyl) trisulfide, 3,3'-bis(diphenyl isopropoxysilylpropyl) tetrasulfide, 3,3'-bis(diphenyl cyclohexoxysilylpropyl) disulfide, 3,3'-bis(dimethyl ethylmercaptosilylpropyl) tetrasulfide, 2,2'-bis(methyl dimethoxysilylethyl) trisulfide, 2,2'-bis(methyl ethoxypropoxysilylethyl) tetrasulfide, 3,3'-bis(diethyl methoxysilylpropyl) tetrasulfide, 3,3'-bis(ethyl di-sec. butoxysilylpropyl) disulfide, 3,3'-bis(propyl diethoxysilylpropyl) disulfide, 3,3'-bis(butyl dimethoxysilylpropyl) trisulfide, 3,3'-bis(phenyl dimethoxysilylpropyl) tetrasulfide, 3-phenyl ethoxybutoxysilyl 3'-trimethoxysilylpropyl tetrasulfide, 4,4'-bis (trimethoxysilylbutyl) tetrasulfide, 6,6'-bis (triethoxysilylhexyl) tetrasulfide, 12,12'-bis (triisopropoxysilyl dodecyl) disulfide, 18,18'-bis (trimethoxysilyloctadecyl) tetrasulfide, 18,18'-bis (tripropoxysilyloctadecenyl) tetrasulfide, 4,4'-bis (trimethoxysilyl-buten-2-yl) tetrasulfide, 4,4'-bis (trimethoxysilylcyclohexylene) tetrasulfide, 5,5'-bis (dimethoxymethylsilylpentyl) trisulfide, 3,3'-bis (trimethoxysilyl-2-methylpropyl) tetrasulfide, 3,3'-bis (dimethoxyphenylsilyl-2-methylpropyl) disulfide.

The preferred sulfur containing organosilicon compounds are the 3,3'-bis(trimethoxy or triethoxy silylpropyl) sulfides. The most preferred compound is 3,3'-bis (triethoxysilylpropyl) tetrasulfide.

Therefore as to the above formula, preferably Z is

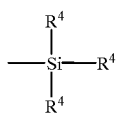

where $R^4$ is an alkoxy of 2 to 4 carbon atoms, with 2 carbon atoms being particularly preferred; Alk is a divalent hydrocarbon of 2 to 4 carbon atoms with 3 carbon atoms being particularly preferred; and n is an integer of from 3 to 5 with 4 being particularly preferred.

The amount of the sulfur containing organosilicon compound of the above formula in a rubber composition will vary depending on the level of silica that is used. Generally speaking, the amount of the sulfur containing organosilicon, compound of, if used, will range from 0.01 to 1.0 parts by weight per part by weight of the silica. Preferably, the amount will range from 0.05 to 0.4 parts by weight per part by weight of the silica.

It is readily understood by those having skill in the art that the rubber composition would be compounded by methods generally known in the rubber compounding art, such as mixing the various sulfur-vulcanizable constituent rubbers with various commonly used additive materials such as, for example, sulfur donors, curing aids, such as activators and retarders and processing additives, such as oils, resins including tackifying resins and plasticizers, fillers, pigments, fatty acid, zinc oxide, waxes, antioxidants and antiozonants and peptizing agents. As known to those skilled in the art, depending on the intended use of the sulfur vulcanizable and sulfur vulcanized material (rubbers), the additives mentioned above are selected and commonly used in conventional amounts. Typical amounts of reinforcing type carbon blacks(s), for this invention, if used, are herein set forth. Representative examples of sulfur donors include elemental sulfur (free sulfur), an amine disulfide, polymeric polysulfide and sulfur olefin adducts. Preferably, the sulfur vulcanizing agent is elemental sulfur. The sulfur vulcanizing agent may be used in an amount ranging from 0.5 to 8 phr, with a range of from 1.5 to 6 phr being preferred. Typical amounts of tackifier resins, if used, comprise about 0.5 to about 10 phr, usually about 1 to about 5 phr. Typical amounts of processing aids comprise about 1 to about 50 phr. Such processing aids can include, for example, aromatic, napthenic, and/or paraffinic processing oils. Typical amounts of antioxidants comprise about 1 to about 5 phr. Representative antioxidants may be, for example, diphenyl-p-phenylenediamine and others, such as, for example, those disclosed in the *Vanderbilt Rubber Handbook* (1978), pages 344—346. Typical amounts of antiozonants comprise about 1 to 5 phr. Typical amounts of fatty acids, if used, which can include stearic acid comprise about 0.5 to about 3 phr. Typical amounts of zinc oxide comprise about 2 to about 5 phr. Typical amounts of waxes comprise about 1 to about 5 phr. Often microcrystalline waxes are used. Typical amounts of peptizers comprise about 0.1 to about 1 phr. Typical peptizers may be, for example, pentachlorothiophenol and dibenzamidodiphenyl disulfide.

In one aspect of the present invention, the rubber composition containing the bis(hydroxyalkyl alkyl ester) polysulfide is sulfur-cured or vulcanized.

Accelerators are used to control the time and/or temperature required for vulcanization and to improve the properties of the vulcanizate. In one embodiment, a single accelerator system may be used, i.e., primary accelerator. The primary accelerator(s) may be used in total amounts ranging from about 0.5 to about 4, preferably about 0.8 to about 1.5, phr. In another embodiment, combinations of a primary and a secondary accelerator might be used with the secondary accelerator being used in smaller amounts, such as from about 0.05 to about 3 phr, in order to activate and to improve the properties of the vulcanizate. Combinations of these accelerators might be expected to produce a synergistic effect on the final properties and are somewhat better than those produced by use of either accelerator alone. In addition, delayed action accelerators may be used which are not affected by normal processing temperatures but produce a satisfactory cure at ordinary vulcanization temperatures. Vulcanization retarders might also be used. Suitable types of accelerators that may be used in the present invention are amines, disulfides, guanidines, thioureas, thiazoles, thiurams, sulfenamides, dithiocarbamates and xanthates. Preferably, the primary accelerator is a sulfenamide. If a second accelerator is used, the secondary accelerator is preferably a guanidine, dithiocarbamate or thiuram compound.

The rubber compositions of the present invention may contain a methylene donor and a methylene acceptor. The term "methylene donor" is intended to mean a compound capable of reacting with a methylene acceptor (such as resorcinol or its equivalent containing a present hydroxyl group) and generate the resin in-situ. Examples of methylene donors which are suitable for use in the present invention include hexamethylenetetramine, hexaethoxymethylmelamine, hexamethoxymethylmelamine, lauryloxymethylpyridinium chloride, ethoxymethylpyridinium chloride, trioxan hexamethoxymethylmelamine, the hydroxy groups of which may be esterified or partly esterified, and polymers of formaldehyde such as paraformaldehyde. In addition, the methylene donors may be N-substituted oxymethylmelamines, of the general formula:

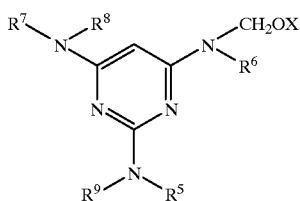

wherein X is an alkyl having from 1 to 8 carbon atoms, $R^5$, $R^6$, $R^7$, $R^8$ and $R^9$ are individually selected from the group consisting of hydrogen, an alkyl having from 1 to 8 carbon atoms and the group —$CH_2$ OX. Specific methylene donors include hexakis-(methoxymethyl)melamine, N,N',N''-trimethyl/N,N', N''-trimethylolmelamine, hexamethylolmelamine, N,N',N''-dimethylolmelamine, N-methylolmelamine, N,N'-dimethylolmelamine, N,N',N''-tris(methoxymethyl)melamine and N,N'N''-tributyl-N,N', N''-trimethylol-melamine. The N-methylol derivatives of melamine are prepared by known methods.

The amount of methylene donor and methylene acceptor that is present in the rubber stock may vary. Typically, the amount of methylene donor and methylene acceptor that each is present will range from about 0.1 phr to 10.0 phr. Preferably, the amount of methylene donor and methylene acceptor that each is present ranges from about 2.0 phr to 5.0 phr.

The weight ratio of methylene donor to the methylene acceptor may vary. Generally speaking, the weight ratio will range from about 1:10 to about 10:1. Preferably, the weight ratio ranges from about 1:3 to 3:1.

The mixing of the rubber composition can be accomplished by methods known to those having skill in the rubber mixing art. For example the ingredients are typically mixed in at least two stages, namely at least one non-productive stage followed by a productive mix stage. The final curatives including sulfur vulcanizing agents are typically mixed in the final stage which is conventionally called the "productive" mix stage in which the mixing typically occurs at a temperature, or ultimate temperature, lower than the mix temperature(s) than the preceding non-productive mix stage (s). The rubber, fillers, bis(hydroxyalkyl alkyl ester) polysulfide and are mixed in one or more non-productive mix stages. The terms "non-productive" and "productive" mix stages are well known to those having skill in the rubber mixing art.

When the rubber compound contains a bis(hydroxyalkyl alkyl ester) polysulfide, silica, as well as a sulfur-containing organosilicon compound, if used, the rubber compound may be subjected to a thermomechanical mixing step. The thermomechanical mixing step generally comprises a mechanical working in a mixer or extruder for a period of time suitable in order to produce a rubber temperature between 140° C. and 190° C. The appropriate duration of the thermomechanical working varies as a function of the operating conditions and the volume and nature of the components. For example, the thermomechanical working may be from 1 to 20 minutes.

Vulcanization of the rubber composition of the present invention is generally carried out at conventional temperatures ranging from about 100° C. to 200° C. Preferably, the vulcanization is conducted at temperatures ranging from about 110° C. to 180° C. Any of the usual vulcanization processes may be used such as heating in a press or mold, heating with superheated steam or hot air or in a salt bath.

Upon vulcanization of the sulfur vulcanized composition, the rubber composition of this invention can be used for various purposes. For example, the sulfur vulcanized rubber composition may be in the form of a tire, belt or hose. In case of a tire, it can be used for various tire components. Such tires can be built, shaped, molded and cured by various methods which are known and will be readily apparent to those having skill in such art. Preferably, the rubber composition is used in the tread of a tire. As can be appreciated, the tire may be a passenger tire, aircraft tire, truck tire and the like. Preferably, the tire is a passenger tire. The tire may also be a radial or bias, with a radial tire being preferred.

The invention may be better understood by reference to the following examples in which the parts and percentages are by weight unless otherwise indicated.

The following examples are presented in order to illustrate but not limit the present invention.

Cure properties were determined using a Monsanto oscillating disc rheometer which was operated at a temperature of 150° C. and at a frequency of 11 hertz. A description of oscillating disc rheometers can be found in the Vanderbilt Rubber Handbook edited by Robert O. Ohm (Norwalk, Conn., R. T. Vanderbilt Company, Inc., 1990), pages 554–557. The use of this cure meter and standardized values read from the curve are specified in ASTM D-2084. A typical cure curve obtained on an oscillating disc rheometer is shown on page 555 of the 1990 edition of the Vanderbilt Rubber Handbook.

In such an oscillating disc rheometer, compounded rubber samples are subjected to an oscillating shearing action of constant amplitude. The torque of the oscillating disc embedded in the stock that is being tested that is required to oscillate the rotor at the vulcanization temperature is measured. The values obtained using this cure test are very significant since changes in the rubber or the compounding recipe are very readily detected. It is obvious that it is normally advantageous to have a fast cure rate.

The invention may be better understood by reference to the following examples in which the parts and percentages are by weight unless otherwise indicated.

EXAMPLE 1

Preparation of bis(hydroxyethyl propylate) disulfide

A 2-liter round-bottom 3-neck flask was equipped with a mechanical stirrer, thermocouple and a water condenser mounted with a dropping funnel. The reaction flask was swept with nitrogen and charged with 105 g (0.50 mole) of 3,3'-dithiodipropionic acid, 62 g (1.0 mole) of ethylene glycol, 22 g of p-toluenesulfonic acid and 260 ml of mixed xylenes. The flask was flushed with nitrogen and sealed under a nitrogen balloon, attached to a Dean-Stark trap for removing water. The flask was heated to 145° C. for 15 minutes, wherein 25 ml of water was removed. The flask was cooled and the volatiles stripped under a reduced pressure of 29 inches of mercury vacuum. Infrared spectroscopy showed loss of the acid functions and formation of the diester. The product was confirmed by Field Desorption Mass Spectrometric analysis which showed the presence of the $S_2$ polysulfides. The liquid product was homogeneously dispersed on carbon black in a 1:1 parts by weight ratio.

EXAMPLE II

In this example, the bis(hydroxyethyl propylate) disulfide prepared in Example 1 was evaluated in comparison with a commercially-available silica coupling agent, namely, bis-(3-triethoxysilylpropyl)tetrasulfide.

Rubber compositions containing the materials set out in Tables 1 and 2 were prepared in a BR Banbury™ mixer using three separate stages of addition (mixing), namely, two non-productive mix stages and one productive mix stage. The first non-productive stage was mixed for up to 4 minutes or to a rubber temperature of 160° C. whichever occurred first. The second non-productive stage was a repeat of the first mixing stage. The mixing time for the productive stage was to a rubber temperature of 120° C. for 2 minutes.

The rubber compositions are identified herein as Samples 1–3. Samples 1 and 2 are considered herein as being controls without the use of a bis(hydroxyalkyl alkyl ester) polysulfide added during the nonproductive mixing stage.

The samples were cured at about 150° C. for about 18 minutes.

Table 2 illustrates the behavior and physical properties of the cured samples 1–3.

It is clearly evident from the results that the use of bis(hydroxyalkyl alkyl ester) polysulfides in Sample 3 as compared to the control Sample 1 gave high stress-strain modulus, higher hardness, higher rebound and improved abrasion resistance. It also gave higher modulus and lower Tan delta as measured by the Rheovibron. Each of these properties are considered important for rubber compound applications.

TABLE 1

|  | Ex. 1 | Ex. 2 | Ex. 3 |
| --- | --- | --- | --- |
| First Non-Productive |  |  |  |
| Cis-1,4-polyisoprene rubber[1] | 100 | 100 | 100 |
| Carbon Black | 15 | 15 | 15 |
| Silica[2] | 20 | 20 | 20 |
| Processing Oil | 5 | 5 | 5 |
| Zinc Oxide | 5 | 5 | 5 |
| Fatty Acid | 2 | 2 | 2 |
| Antioxidant[3] | 2 | 2 | 2 |
| Silane Coupling Agent[4] | 0 | 3 | 0 |
| Bis (hydroxyethyl propylate) disulfide[5] | 0 | 0 | 5 |
| Second Non-Productive |  |  |  |
| Silica | 15 | 15 | 15 |
| Silane Coupling Agent | 0 | 2 | 0 |
| Productive |  |  |  |
| Sulfur | 1.5 | 1.5 | 1.5 |
| Accelerator, sulfenamide type | 2 | 2 | 2 |

TABLE 1-continued

|  | Ex. 1 | Ex. 2 | Ex. 3 |
| --- | --- | --- | --- |
| Accelerator, diphenylguanidine | 0.5 | 0.5 | 0.5 |

[1]Synthetic cis-1,4-polyisoprene rubber (NAT2200) from The Goodyear Tire & Rubber Company.
[2]Silica obtained as Hi-Sil 210 from PPG Industries, Inc.
[3]Of the polymerized 1,2-dihydro-2,2,4-trimethylquinoline type
[4]Obtained as bis-(3-triethoxysilylpropyl) tetrasulfide, which is commerically available as X50S from Degussa Gmbh and is provided in a 50/50 by weight blend with carbon black.
[5]As prepared in Example 1, 50/50 by weight blend with carbon black.

TABLE 2

| Samples | 1 | 2 | 3 |
| --- | --- | --- | --- |
| Bis(hydroxyethyl propylate) disulfide | 0 | 0 | 5 |
| Bis-(3-triethoxysilylpropyl) tetrasulfide | 0 | 5 | 0 |
| Rheometer, 150° C. |  |  |  |
| Max Torque | 41.5 | 44.6 | 43.3 |
| Min Torque | 12.0 | 8.0 | 8.7 |
| Delta Torque | 29.5 | 36.6 | 34.6 |
| T90 | 19.0 | 16.3 | 19.0 |
| T25 | 15.3 | 12.8 | 14.0 |
| Stress Strain 36' @ 150° C. |  |  |  |
| 100% M (MPa) | 1.27 | 2.69 | 2.11 |
| 300% M (MPa) | 4.28 | 11.01 | 7.10 |
| Tensile Strength (MPa) | 20.0 | 22.2 | 18.6 |
| Elongation @ Break (%) | 723 | 562 | 595 |
| Hardness, RT | 56.1 | 65.5 | 64.9 |
| 100 C. | 52.8 | 64.8 | 63.7 |
| Rebound, RT | 45.3 | 52.5 | 51.4 |
| 100 C. | 59.0 | 66.8 | 62.3 |
| Rheovibron, 60° C. |  |  |  |
| E', MPa | 13.9 | 18.6 | 21.6 |
| Tan Delta | 0.070 | 0.055 | 0.054 |
| DIN Abrasion (lower is better) | 225 | 128 | 172 |
| Strebler Adhesion (95° C.) | 212 | 63 | 117 |

While certain representative embodiments and details have been shown for the purpose of illustrating the invention, it will be apparent to those skilled in this art that various changes and modifications may be made therein without departing from the spirit or scope of the invention.

What is claimed is:

1. A rubber composition comprising an elastomer containing olefinic unsaturation and a bis(hydroxyalkyl alkyl ester) polysulfide of the formula

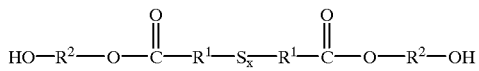

where $R^1$ is independently selected from alkylene groups having 1 to 8 carbon atoms, $R^2$ is independently selected from alkylene groups having 2 to 6 carbon atoms and x is an integer of from 2 to 8.

2. The composition of claim 1 wherein said bis (hydroxyalkyl alkyl ester) polysulfide is present in an amount ranging from 0.05 to 10.0 phr.

3. The composition of claim 1 wherein $R^1$ is an alkylene group having from 1 to 6 carbon atoms, $R^2$ is an alkylene group having from 2 to 4 carbon atoms and x is an integer of from 2 to 4.

4. The composition of claim 1 wherein a sulfur containing organosilicon compound is present and is of the formula:

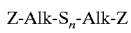

in which Z is selected from the group consisting of

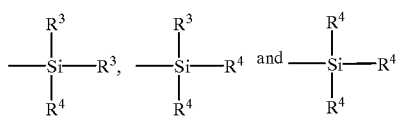

where $R^3$ is an alkyl group of 1 to 4 carbon atoms, cyclohexyl or phenyl;

$R^4$ is alkoxy of 1 to 8 carbon atoms, or cycloalkoxy of 5 to 8 carbon atoms;

Alk is a divalent hydrocarbon of 1 to 18 carbon atoms and n is an integer of 2 to 8.

5. The composition of claim 1 wherein a filler is present in an amount ranging from 10 to 250 phr.

6. The composition of claim 5 wherein said filler is silica and said silica filler is used in an amount ranging from 15 to 80 phr.

7. The composition of claim 6 wherein sulfur containing organosilicon compound is present in an amount ranging from 0.01 to 1.0 parts by weight per part by weight of said silica.

8. The composition of claim 5 wherein said filler is carbon black and said carbon black is used in an amount ranging from 1 to 80 phr.

9. The composition of claim 1 wherein said elastomer containing olefinic unsaturation is selected from the group consisting of natural rubber, neoprene, polyisoprene, butyl rubber, polybutadiene, styrene-butadiene copolymer, styrene/isoprene/butadiene rubber, methyl methacrylate-butadiene copolymer, isoprene-styrene copolymer, methyl methacrylate-isoprene copolymer, acrylonitrile-isoprene copolymer, acrylonitrile-butadiene copolymer, EPDM and mixtures thereof.

10. A sulfur vulcanized rubber composition which is prepared by heating the composition of claim 1 to a temperature ranging from 100° C. to 200° C. in the presence of a sulfur vulcanizing agent.

11. The sulfur vulcanized rubber composition of claim 10 in the form of a tire, belt or hose.

12. A tire having a tread comprised of the composition of claim 10.

* * * * *